United States Patent [19]

Arena

[11] 4,382,150

[45] May 3, 1983

[54] METHOD FOR HYDROGENATING AQUEOUS SOLUTIONS OF CARBOHYDRATES

[75] Inventor: Blaise J. Arena, Des Plaines, Ill.

[73] Assignee: UOP Inc., Des Plaines, Ill.

[21] Appl. No.: 340,614

[22] Filed: Jan. 19, 1982

[51] Int. Cl.$^3$ .................... C07C 31/18; C07C 31/24; C07C 31/26

[52] U.S. Cl. .................................................. 568/863

[58] Field of Search ........................................ 568/863

[56] References Cited

U.S. PATENT DOCUMENTS 3,055,840  9/1962  Koch .................................. 568/881

FOREIGN PATENT DOCUMENTS 354196  8/1931  United Kingdom ................ 568/863

*Primary Examiner*—Joseph E. Evans
*Attorney, Agent, or Firm*—James R. Hoatson, Jr.; Eugene I. Snyder; William H. Page, II

[57] ABSTRACT

Zerovalent Group VIII metals dispersed on titanium dioxide reduced and calcined at a temperature less than about 300° C. are hydrothermally stable hydrogenation catalysts which may be used advantageously in the reduction of aqueous solutions of carbohydrates. The use of nickel on titanium dioxide in the hydrogenation of glucose affords sorbitol in excellent yields with quite high selectivity.

10 Claims, No Drawings

METHOD FOR HYDROGENATING AQUEOUS SOLUTIONS OF CARBOHYDRATES

BACKGROUND OF THE INVENTION

In hydrogenating organic material using zerovalent metal catalysts, it is more common to use the metal dispersed on an inert support than to use, for example, colloidal dispersions of the metal itself. Among advantages accruing to supported metals are included their greater surface activity, leading to increased reactivity, and their greater ease of separation, as by filtration. Colloidal metals are notoriously difficult to separate by filtration, and incomplete removal and recovery is costly and often deleterious to the product of hydrogenation.

When hydrogenations are conducted in aqueous media, the lack of hydrothermal stability of the commonly used supports places severe limitations on catalyst lifetime and recovery and also on the quality of the product due to dissolved support material. Where such hydrogenations are of hydroxylic organic compounds, the problem of hydrothermal instability of support materials is intensified. Where the organic compounds are polyhydroxylic, such as carbohydrates, the problem of hydrothermal instability is particularly exacerbated because of the relatively high concentration of hydroxyl groups from both water as solvent and the material to be hydrogenated.

The irony in hydrogenating aqueous solutions of carbohydrates is two-fold. First, the reduction products of many carbohydrates are important materials of commerce; sorbitol and mannitol are but two common reduction products. Additionally, there is no practical alternative to using water as the solvent in hydrogenating carbohydrates because carbohydrates generally are insoluble or, at best, sparingly soluble in most organic solvents. And because carbohydrates are solids, it is operationally mandatory to use a solvent in their hydrogenation.

Therefore, it is an object of this invention to hydrogenate carbohydrates in aqueous media using as a catalyst a zerovalent metal on a hydrothermally stable support. An embodiment comprises a method of hydrogenating an aqueous solution of a carbohydrate where the catalyst is a Group VIII zerovalent metal dispersed on a support of titanium dioxide, $TiO_2$. In a more specific embodiment, the metal is nickel. In a still more specific embodiment, the nickel on titanium dioxide combination is reduced at a temperature less than about 300° C. In a yet more specific embodiment, the carbohydrate is a hexose.

DESCRIPTION OF THE INVENTION

The invention which is the subject matter herein is a method for the hydrogenation of a carbohydrate to its polyols comprising contacting at hydrogenation conditions an aqueous solution of the carbohydrate with hydrogen and a catalyst consisting essentially of a zeovalent Group VIII metal selected from the group consisting of cobalt, nickel, ruthenium, palladium and platinum dispersed on titanium dioxide, and recovering the formed polyols. This invention results from the discovery that titanium dioxide possesses remarkable hydrothermal stability under conditions necessary for the hydrogenation of aqueous solutions of carbohydrates. Thus, whereas substantial amounts of silica and alumina, which are to commonly employed support materials, dissolve in the aqueous medium during hydrogenation of carbohydrates, virtually no leaching of titanium dioxide occurs under comparable hydrogenation conditions.

Therefore, one advantage of this invention is that the product contains a substantially lower level of dissolved metal from the inert support described herein than that resulting from inert supports commonly employed previously in the hydrogenation of carbohydrates.

Another advantage of this invention is that the zerovalent metals commonly employed as a hydrogenation catalyst retain their activity on the titanium dioxide support of this invention.

Still another advantage is that the results of hydrogenation may be altered by changing the temperature of reduction of the metal on titanium dioxide. Thus, one may exert control over the product distribution by the novel technique of changing the reduction temperature.

As mentioned previously, the invention herein is concerned with a method of hydrogenating a carbohydrate to its polyols. Carbohydrates are polyhydroxyaldehydes, polyhydroxyketones, or compounds that can be hydrolyzed to them. A carbohydrate that cannot be hydrolyzed to simpler compounds is called a monosaccharide. One that can be hydrolyzed to two monosaccharide molecules is called a disaccharide, and one that can be hydrolyzed to many monosacchride molecules is called a polysaccharide. A monosaccharide may be classified according to the number of carbon atoms it contains; a hexose is a 6-carbon monosaccharide, a pentose is a 5-carbon monosaccharide, and a tetrose is a 4-carbon monosaccharide. Monosaccharides are preferred among the carbohydrates which may be used in this invention. Among the monosaccharides the hexoses, pentoses and tetroses are the most important members, with the hexoses particularly preferred.

The polyol reduction products of this invention have the formula $HOCH_2(CHOH)_nCH_2OH$, where n is 2, 3, or 4 depending upon the kind of monosaccharide used or the kind of units in the di- or polysaccharide. Where n is 4, the polyol is a hexitol; where n is 3, the polyol is a pentitol; and where n is 2, polyol is a tetritol. It is to be understood that where the carbohydrate is a disaccharide or polysaccharide, substantial hydrolysis accompanies hydrogenation to ultimately afford the polyols of this invention.

The examples of carbohydrates are cited merely for illustration, and are not intended as exhaustive of the suitable reactants which may be used in this invention. Accordingly, monosaccharides that can be employed include glucose, mannose, galactose, talose, fructose, allose, altrose, idose, gulose, xylose, lyxose, ribose, arabinose, threose and erythrose. Glucose and mannose are particularly preferred monosaccharides which afford sorbitol and mannitol, respectively, as their polyol reduction product. Fructose is another preferred monosaccharide and affords a mixture of sorbitol and mannitol as the product. Examples of disaccharides include maltose, cellobiose, sucrose and lactose. Among the more abundant polysaccharides which may be employed in this invention are starch, cellulose and their degradation products.

The catalysts of this invention consist essentially of a zerovalent Group VIII metal dispersed on titanium dioxide. Among the metals which may be used are included cobalt, nickel, ruthenium, palladium and platinum, with nickel being preferred chiefly because of its relatively low cost.

The Group VIII metal is generally dispersed on titanium dioxide as the inert support by impregnating the latter with a suitable salt of the metal, calcining the salt where necessary, followed by reduction to the zerovalent metal in a hydrogen atmosphere. Calcining is performed where volatiles are to be removed from the support, or where the metal salt needs to be converted, e.g., to its oxide, to be readily reducible. In suitable cases calcination and reduction may be combined in the same step. The temperature of reduction has a substantial influence on the catalyst in the process of this invention. Thus, it has been found that where reduction is performed at a temperature less than about 300° C., the resulting catalyst effects maximum conversion of the carbohydrate with maximum formation of its polyol hydrogenation product. The lower limit of reduction temperature is not critical and is dictated by the desire to have a reasonable rate for reduction of the metal. It is preferred that the temperature be from about 100° to about 300° C. with a temperature from about 150° to about 250° C. being even more desirable. Where the reduction temperature used in the preparation of the catalyst is greater than about 300° C., the resulting catalyst often causes isomerization of the carbohydrate and somewhat lower hydrogenation activity. Thus, for example, when a nickel-titania catalyst reduced at 450° C. is used in the hydrogenation of glucose, its isomerization product, fructose, is formed in substantial amounts together with mannitol (a reduction product of fructose) and sorbitol (a reduction product of both fructose and glucose). The amount of metal on titanium dioxide is not particularly critical. When nickel is used, concentrations from about 1 to about 25 percent by weight nickel are commonly employed.

The aqueous solution of the carbohydrate is contacted with hydrogen and the catalyst of this invention at hydrogenation conditions. Hydrogenation conditions include a pressure of at least about 200 psig, with pressures in excess of about 2500 psig generally not advantageous. In the usual case, a hydrogen pressure from about 500 to about 2000 psig is used. The hydrogenation temperature will be greater than about 80° C., with the upper temperature limit dictated by the onset of the decomposition of either the product or reactant. For example, in the case of glucose as the reactant and sorbitol as the product, the upper temperature limit is about 160° C. In practical terms, a hydrogenation temperature from about 100° to about 150° C. is preferred.

The amount of catalyst used will depend, inter alia, on the amount of nickel on the support, hydrogenation pressure, and temperature. Generally, sufficient catalyst is employed to give from about 0.2 to about 3.0 wt. % nickel based on the carbohydrate as monosaccharide.

The method of this invention may be practiced in either a batch or a fixed mode. In the batch mode, an aqueous solution of the carbohydrate containing from about 5 to about 50 percent carbohydrates is loaded into a reactor containing the nickel on titanium dioxide catalyst of this invention in an amount sufficient to give from about 0.2 to about 3.0 wt. % nickel based on the carbohydrate. The mixture is then heated to the desired temperature, which is from about 100° to about 150° C. After the desired reaction temperature is attained, hydrogen is admitted to a pressure of from about 500 to 2000 psig. The entire reaction mixture is then agitated to provide adequate contact among the hydrogen, catalyst, and carbohydrate. The hydrogenation is continued until there is no further hydrogen uptake, which generally is a time from about 1 to about 6 hours.

The examples which follow merely illustrate this invention and are not intended to limit it in any way.

EXAMPLE I 29.2 g of nickel nitrate hexahydrate was dissolved in 150 ml of deionized water. This solution was added to 53 g of TiO$_2$ support and mixed for 0.5 hr. The solution was then steam evaporated leaving the TiO$_2$ impregnated with nickel nitrate. A portion of this material was calcined in air for 2.5 hrs. at 450° C. followed by reduction in hydrogen at 450° C. for 2.5 hrs. A second portion of the impregnated material was calcined in air at 250° C. for 2.5 hrs. followed by reduction in hydrogen at 250° C. for 2.5 hrs. In both cases the catalysts were stored under N$_2$.

EXAMPLE II

The following experiment was done to demonstrate the hydrothermal stability of various materials often used as an inert support for catalytically active zerovalent metals. A mixture of 50 ml of a 50 percent aqueous solution of sorbitol and 2.5 g of support material was held in a rotating glass-lined autoclave for 24 hours in the presence of hydrogen at 135 atmospheres and at 130° C. At the end of this period, solid was removed by filtration and the filtrate was analyzed for metals. The following table summarizes the results.

| LEACHING OF INERT SUPPORTS | |
|---|---|
| Support Material | Dissolved Support Material |
| TiO$_2$-bentonite (~90% TiO$_2$) | less than 1 ppm Ti; 93 ppm Si |
| gamma-alumina[a] | 60 ppm Al |
| gamma-alumina[b] | 129 ppm Al |
| kiselguhr[c] | 83 ppm Si |

[a] 0.5 ABD, SA 200 m$^2$/g
[b] 0.3 ABD, SA 160 m$^2$/g
[c] Solution of glucose was used instead of sorbitol.

The results clearly show the superior hydrothermal stability of titanium dioxide relative to other commonly employed supports.

EXAMPLE III

A mixture of 60 ml of a 45 percent aqueous solution of glucose containing 6 g of a 10 percent nickel on titanium dioxide catalyst, reduced at 250° C., was reacted with hydrogen at 700 psig and 120° C. for 5 hours. The cooled reaction mixture was then analyzed by high pressure liquid chromatography which showed that 98 percent of the glucose had reacted to afford as the only two products sorbitol and mannitol with selectivity of 95 percent and 3 percent respectively.

EXAMPLE IV

This hydrogenation was conducted as that described above except that the catalyst was a nickel on titanium dioxide which had been reduced at 450° C. Analysis showed only 63 percent glucose conversion to afford sorbitol, mannitol, and fructose in selectivity of 44, 4, and 27 percent respectively.

What is claimed is:

1. A method for the hydrogenation of a carbohydrate in aqueous solution to its polyols comprising contacting at hydrogenation conditions a reaction medium consisting essentially of said solution with hydrogen and a catalyst consisting essentially of nickel dispersed on titanium dioxide, and recovering the formed polyols.

2. The method of claim 1 where the carbohydrate is a monosaccharide.

3. The method of claim 2 where the monosaccharide is selected from the group consisting of hexoses, pentoses, and tetroses.

4. The method of claim 3 where the monosaccharide is a hexose and the polyol is a hexitol.

5. The method of claim 4 where the hexose is glucose or mannose and the hexitol is sorbitol or mannitol, respectively.

6. The method of claim 4 where the hexose is fructose and the polyol is a mixture of sorbitol and mannitol.

7. The method of claim 1 where the nickel-titanium dioxide combination has been reduced at a temperature less than about 300° C.

8. The method of claim 1 where the hydrogenation conditions include a hydrogen pressure from about 200 to about 2500 psig and a temperature from about 80° to about 160° C.

9. The method of claim 8 where the pressure is from about 500 to about 2000 psig.

10. The method of claim 8 where the temperature is from about 100° to about 150° C.

* * * * *